US007485317B1

(12) United States Patent  
Murayama et al.

(10) Patent No.: US 7,485,317 B1
(45) Date of Patent: Feb. 3, 2009

(54) THERMO-REVERSIBLE POLYMER FOR INTRALUMENAL IMPLANT

(75) Inventors: Yuichi Murayama, Tokyo (JP); Fernando Vinuela, Los Angeles, CA (US); Yuichi Mori, Yamanashi-ken (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/890,799

(22) PCT Filed: Feb. 5, 1999

(86) PCT No.: PCT/US99/02445

§ 371 (c)(1),
(2), (4) Date: Jan. 2, 2002

(87) PCT Pub. No.: WO00/45868

PCT Pub. Date: Aug. 10, 2000

(30) Foreign Application Priority Data

Feb. 9, 1999 (EP) .................................. 99400301

(51) Int. Cl.
*A61F 2/02* (2006.01)
*A61K 9/14* (2006.01)
(52) U.S. Cl. .................. 424/423; 424/484; 424/486
(58) Field of Classification Search ................ 424/422, 424/423, 484, 486, 487, 488
See application file for complete search history.

(56) References Cited

U.S. PATENT DOCUMENTS 5,407,445 A * 4/1995 Tautvydas et al. ............. 623/8
5,575,815 A * 11/1996 Slepian et al. ............... 600/36

FOREIGN PATENT DOCUMENTS

| EP | 0724888 A1 * | 8/1996 |
| EP | A 0 724 888 | 8/1996 |
| WO | 97 05185 A | 2/1997 |
| WO | 98 24427 A | 6/1998 |

* cited by examiner

*Primary Examiner*—Carlos A. Azpuru
(74) *Attorney, Agent, or Firm*—Stefan J. Kirchanski; Venable LLP

(57) ABSTRACT

An intralumenal implant material, which comprises, a polymer having a sol-gel transition temperature in an aqueous solution thereof, shows a substantial water-insolubility at a temperature higher than the sol-gel transition temperature, and shows a thermo-reversible water-solubility at a temperature lower than the sol-gel transition temperature. Such an intralumenal implant is capable to be endovascularly or percutaneuosly delivered into a vascular lumen in a liquid state at the temperature lower than the sol-gel transition temperature, is capable to be instantly converted into a gel state in the vascular lumen at the blood temperature higher than the sol-gel transition temperature and is capable of occluding aneurysms, vascular tumors or vascular malformation. Such intralumenal implant material shows excellent biocompatibility and mechanical matching for the vascular tissue and the surrounding tissue because it is a highly water-containing hydrogel. In addition, biologically active substances for promoting a prompt neo-endothelium formation and/or endothelialization can be easily incorporated into such an intralumenal implant material.

13 Claims, 2 Drawing Sheets

Pre-embolization**

Post-embolization**

THERMO-REVERSIBLE POLYMER FOR INTRALUMENAL IMPLANT

BACKGROUND OF THE INVENTION

1. Field of the Invention

The present invention is in the general field of surgical and endovascular interventional instruments, and relates particularly to intralumenal implants to occlude vessels or aneurysms. More specifically, the present invention relates to intralumenal implants for vascular lesions of vertebral bodies and/or intervertebral discs to gain disc stability and to eliminate discogenic pain.

2. Description of Related Art

There are a number of medical situations where it is desirable to occlude various elements of the vascular system. For example, vascular abnormalities such as arterio-venous malformation (AVM) and arterio-venous fistulae may form aneurysms that gradually increase in size only to eventually burst causing a catastrophic bleed particularly if the bleed occurs in the brain. Various metallic coils made of biocompatible elements such as platinum, gold and tungsten are presently used as intralumenal implants for occlusion of body arteries and veins, brain aneurysms, and vascular malformation. These radiopaque coils are typically placed at the desired site within a vascular lumen, percutaneously or through a microcatheter.

The coils occlude vessels or aneurysms by filling the lumen and acting as a physical barrier to blood flow. Ultimately the coils promote thrombus formation that further limits blood flow. Permanent occlusion of vessels or aneurysms requires the formation of an intralumenal thrombus that induces scar formation and the formation of neo-endothelium across the neck of aneurysms.

However, conventional coils are often not sufficient to form and mature thrombus the within aneurysms. As a result, conventional coils often do not appear to promote prompt endothelialization across the neck of aneurysms. This problem is most obvious in small aneurysms with a wide neck and in large or giant aneurysms. To solve this shortcoming of conventional intralumenal implants such as metallic coils, intralumenal implants of liquid embolic agents have been developed. One such material is composed of liquid cyanoacrylate monomer that rapidly polymerizes into a solid upon contacting a trace amount of water. Although cyanoacrylate can work rapidly it has certain drawbacks: 1) Polycyanoacrylate is so rigid to cause a harmful mechanical damage to surrounding soft vascular tissue; 2) both cyanoacrylate monomer and the byproducts of polymerization are toxic; 3) When cyanoacrylate is injected into a vascular by a catheter, there is no contact with water until the cyanoacrylate leaves the tip of the catheter where it instantly solidifies fixing the tip of the catheter and making withdrawal of the catheter difficult; 4) Because biologically active substances such as cytokines are not miscible with cyanoacrylate, it is impossible to load them into the occlusive agent. The last shortcoming is significant because biologically active substances play an important role of promotion of prompt endothelialization, which results in permanent stability of the injected embolic agents.

Another liquid embolic material is fibrin glue. The demerits of fibrin glue are: 1) In order to get fibrin glue to polymerize, a mixing process of fibrinogen aqueous solution and thrombin/calcium chloride aqueous solution is required, thereby making injection into a vascular lumen by catheter difficult; 2) The conversion from fibrinogen to fibrin is too slow for the injected fibrinogen to remain and turn to fibrin before being carried away by the blood flow; and 3) Fibrin glue is susceptible to metabolic destruction (e.g., by plasminogen) so it may not remain long enough for neo-endothelium formation.

Water-insoluble polymers dissolved in organic solvents have also been used as liquid embolic agents. The serious problems of these materials are: 1) Organic solvents such as dimethylsulfoxide are potentially toxic to the vascular walls and the surrounding tissues; and 2) Insolubility of biologically active substances in organic solvents makes loading of biologically active substances virtually impossible.

These problems common to the conventional liquid embolic agents, e.g., poor biocompatibility including toxicity and mechanical mismatching, poor durability, difficult injection mode and poor miscibility of biologically active substances with the conventional liquid embolic agents have hitherto remained unsolved.

OBJECTIVES AND SUMMARY OF THE INVENTION

An object of the present invention is to provide a liquid material for intralumenal implant that is capable of significantly reducing the toxicity caused by organic solvent used in the conventional liquid agents, cyanoacrylate monomer, and the byproducts of cyanoacrylate polymerization.

Another object of the present invention is to provide a liquid material for intralumenal implant which is easily injected and solidifies without the difficulties associated with conventional liquid embolic agents such as the fibrin glue that requires mixing fibrinogen aqueous solution with thrombin/calcium chloride aqueous solution or cyanoacrylate monomer that makes withdrawal of the catheter from the injected site difficult.

A further object of the present invention to provide a liquid for intralumenal implant which solidifies rapidly enough not to avoid being washed away by blood flow.

Yet a further object of the present invention is to provide a liquid for intralumenal implant which allows ready loading of biologically active substances.

An additional object of the present invention is to provide a liquid for intralumenal implant that remains as a solid in the vascular lumen until a neo-endothelium formation has occurred.

A further object of the present invention is to provide an intralumenal implant which minimizes mechanical mismatching with the surrounding soft tissue, that is a material that remains relatively soft and pliable following solidification.

These and other objectives are met by an intralumenal implant that comprises a polymer having a sol-gel transition temperature in an aqueous solution thereof. This polymer shows substantial water-insolubility at a temperature higher than the sol-gel transition temperature, and further shows a substantial water-solubility at a temperature lower than that temperature. A polymer with these characteristics solves the above-described problems common to the conventional intralumenal implant devices such as the metallic coils and the liquid embolic agents.

The material of the present invention comprises, at least, water and a polymer having a sol-gel transition temperature in an aqueous solution thereof. So that the material assumes a liquid state (sol state) at a temperature lower than the sol-gel transition temperature, and assumes a gel state which is substantially water-insoluble at a temperature higher than the sol-gel transition temperature. Further, because the polymer is water soluble, the material of the present invention readily incorporates a wide variety of biologically active substances.

The present invention also provides an intralumenal implant that comprises substances that modulate the sol-gel transition temperature of the polymer and any included biologically active substances. The present invention also provides an intralumenal implant that comprises radiopaque agents.

The intralumenal implant material according to the present invention can be delivered endovascularly or percutaneously into a vascular lumen for occlusion of aneurysms, vascular tumors or vascular malformation in a liquid state (sol state) at a temperature lower than the sol-gel transition temperature, whereupon it instantly turns to a semi-solid state (gel state) in the vascular lumen at a body temperature (e.g. about 37° C.—a temperature higher than the sol-gel transition temperature).

The material for intralumenal implant according to the present invention is safe because it contains no toxic substances such as organic solvents or cyanoacrylate monomer that are found in conventional liquid embolic agents.

The intralumenal implant according to the present invention can significantly overcome difficulties of delivery and solidification seen with conventional liquid embolic agents because the material of the present invention instantly changes from a liquid state (sol state) to a semi-solid state (gel state) upon a temperature increase from a temperature below the sol-gel transition temperature to a temperature above the transition temperature (e.g. the blood temperature). Accordingly, the intralumenal implant material according to the present invention doesn't experience the mixing process of conventional fibrin glue or the difficult withdrawal of the catheter from the vascular lumen The intralumenal implant according to the present invention remains solid at the injected site without being washed away by the blood stream. The material of the present invention more rapidly changes from a liquid state (sol state) to a semi-solid state (gel state) than does fibrin glue which must react to form fibrinogen prior to solidification or than does conventional liquid embolic agents which require replacement of organic solvent with blood to effect solidification, respectively.

The intralumenal implant according to the present invention is able to contain much a larger proportion of biologically active water soluble substances than the conventional liquid embolic agents, because the material contains a lot of water. However, the material of the present invention remains in a vascular lumen until formation of a neo-endothelium and/or endothelialization because the material is composed of a synthetic polymer that cannot be metabolically degraded. The material of the present invention causes no mechanical mismatch with the surrounding soft tissue because the intralumenal implant turns into a semi-solid state (gel) which is soft and elastic due to its high water content.

The above-described characteristics of the intralumenal implant material according to the present invention are based on the fact that the intralumenal implant material has a clear sol-gel transition temperature. The intralumenal implant material is in a liquid state (sol state) at a temperature lower than the sol-gel transition temperature and is in a semi-solid state (gel state) which is substantially water-insoluble at a temperature higher than the sol-gel transition temperature, and that the sol-gel transition is thermally reversible.

These sol-gel properties are achieved by using an organic polymer that comprises a plurality of blocks having a cloud point combined or alternating with hydrophilic blocks combined. The presence polymer blocks having a cloud point imparts the polymer with the property being converted into a hydrophobic state at a temperature higher than the cloud point and of being converted into a hydrophilic state at a temperature lower than the cloud point temperature. This results from the thermodynamic property of hydrophobic bonds increasing in strength with increasing temperature (and conversely decreasing in strength with decreasing temperature). The above-described property of the blocks having a cloud point is caused by hydrophobic bond of the blocks whose strength increases with an increase in temperature and decreases with a decrease in temperature. The "cloud point" represents the temperature at which a water-soluble compound begins to come out of solution with resulting scattering of light or "cloud" formation. In the present invention hydrophobic bonds form between the cloud point blocks replacing the bonds between the blocks and the water molecules, thereby causing the blocks to become insoluble.

The presence of hydrophilic blocks imparts the polymer with the ability to form a water-containing gel rather than being precipitated at a temperature higher than the cloud point temperature due to an excess increase in the hydrophobic bonding strength of the cloud point blocks. The coexistence of the cloud point blocks and the hydrophilic blocks in the polymer causes it to be converted from a water-soluble sol state below the temperature into a water-insoluble gel state at a temperature at or above the cloud point temperature, which temperature essentially corresponds to the sol-gel transition temperature of the polymer.

The novel intralumenal implant material can be delivered endovascularly or percutaneously into a vascular lumen as a liquid (sol state) at a temperature below the sol-gel transition temperature, and occludes the aneurysms, vascular tumors or vascular malformation by instantly gelling at body temperature (e.g., about 37°) which temperature is above the sol-gel transition temperature. Because the blood temperature is in the vicinity of 37° C., the sol-gel transition temperature of the above polymer should be higher than 0° C. and not higher than about 40° C., in view of the maintenance of a stable gel state in a vascular lumen.

According to the present inventors' investigation, it has been found that the above-described problems have been solved by using a polymer having a sol-gel transition temperature in an aqueous solution thereof, assuming a liquid state (sol state) at a temperature lower than the sol-gel transition temperature and assuming a gel state which is substantially water-insoluble at a temperature higher than the sol-gel transition temperature.

DETAILED DESCRIPTION OF THE PREFERRED EMBODIMENTS

Figure 1:
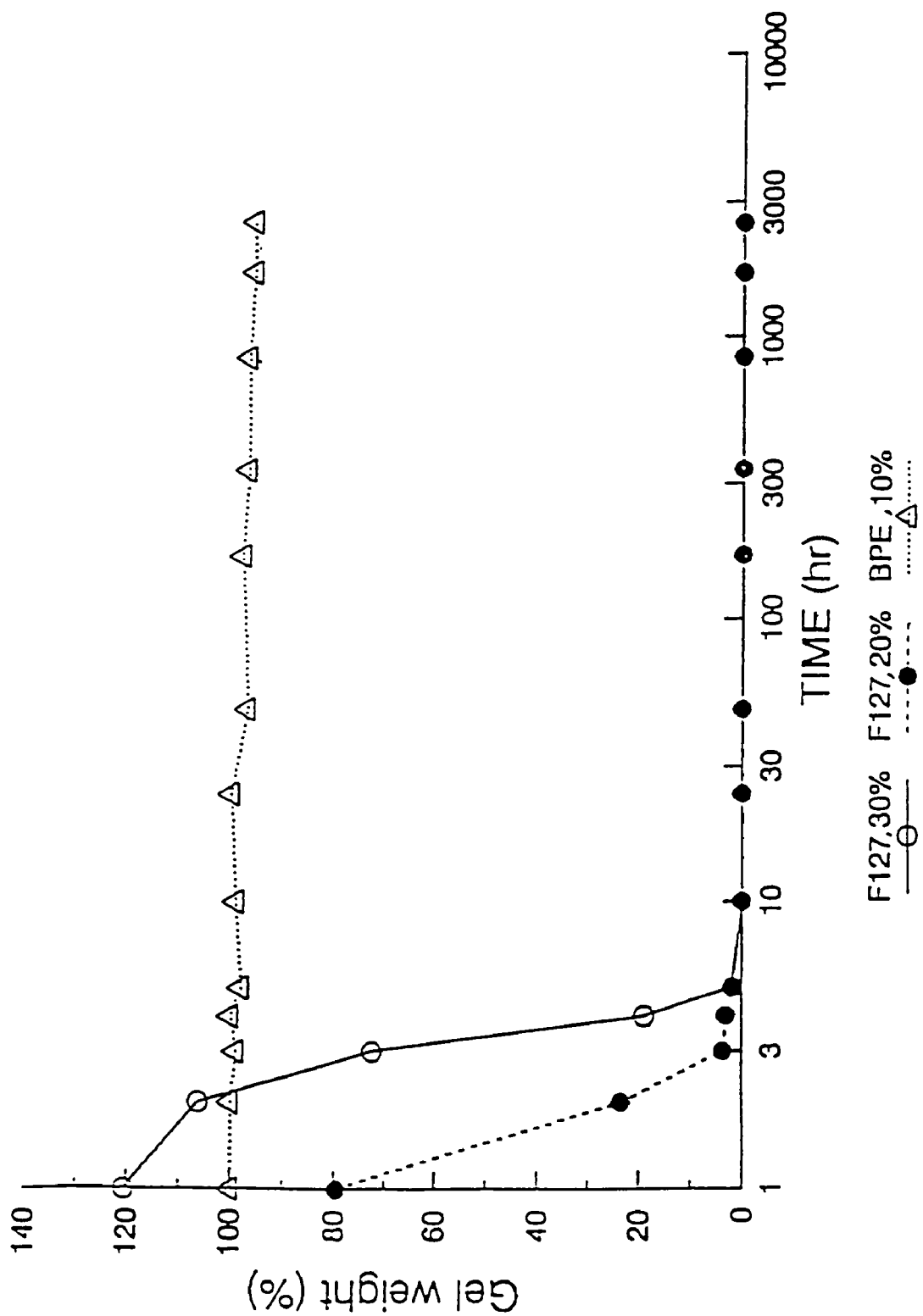
FIG. 1 is a graph showing the results of the measurement of a weight change in water (i.e., measurement of water solubility above the gel temperature) of a polymer (BPE) of the present invention, as compared with a prior art material (Pluronic F-127 gels with concentration of 20%-30%).

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a liquid embolic material for injection into vasculature based on a water soluble organic polymer containing a plurality of blocks having a defined cloud point and a hydrophilic block so that the material is a sol below the cloud point temperature and a gel above that temperature.

Several specific examples of polymers having a sol-gel transition temperature in an aqueous solution thereof and reversibly assuming a sol state at a temperature lower than the sol-gel transition temperature are known. For example, poly-alkylene-oxide block copolymers represented by block copolymers comprising polypropyleneoxide portions and polyethyleneoxide portions; etherified (or ether group-containing) celluloses such as methyl cellulose and hydroxypropyl cellulose; chitosan derivatives, etc. are know to show such properties, (See, K. R. Holme. et al. Macromolecules, 24, 3828 (1991)).

In addition, there has been developed a wound-covering gel (R. M. Nalbandian et al., J. Biomed. Mater. Res., 6, 583 (1972); J. Biomed. Mater. Res., 12, 1135 (1987)) utilizing Pluronic F-127 (trade name, manufactured. by BASF Wyandotte Chemical Co.) each molecule of which comprises a polypropyleneoxide portion with polyethylene oxide portions bonded to the both terminals thereof. It is known that a high-concentration (e.g., 20-30 wt. %) aqueous solution of the above Pluronic F-127 is converted into a hydrogel at a temperature of not lower than about 20° C. and is converted into an aqueous solution at a temperature lower than that temperature. However, this material can assume a gel state only at a high concentration of not lower than about 20 wt. %.

In addition, even when such a gel having a high concentration of not lower than about 20 wt. % is maintained at a temperature of not lower than the gel-forming temperature, the gel can be dissolved by further adding water thereto. When a gel comprising PLURONIC F-127 is formed in a vascular lumen at body temperature of about 37° C., the blood dissolves the gel. Therefore it is difficult to maintain a stable gel state in the vascular lumen making it impossible to occlude aneurysms, vascular tumors or vascular malformation. In addition, because the molecular weight of the Pluronic F-127 is relatively low, it shows an extremely high osmotic pressure at high concentrations. Simultaneously the Pluronic F-127, which is a potent detergent or wetting agent, easily permeates the cell membranes, whereby the Pluronic F-127 can adversely affect cellular elements.

On the other hand, in the case of an etherified cellulose represented by methyl cellulose, hydroxypropyl cellulose, etc., the sol-gel transition temperature thereof is as high as about 45° C. or higher (See, N. Sarkar, J. Appl. Polym. Science, 24, 1073, (1979)). Accordingly, when such etherified cellulose is delivered in a vascular lumen, because the temperature of the blood is, at most, 37° C., the polymer assumes a sol state and is carried away by the blood, whereby the polymer cannot occlude the aneurysms, vascular tumors or vascular malformation.

Further, the above-mentioned chitosan derivatives have a sol-gel transition temperature as high as about 50° C. (See, K. R. Holme. et al., Macromolecules, 24, 3828 (1991)). When such a chitosan derivative is delivered in a vascular lumen, it remains in the sol state and is carried away by the blood.

As described above, when a conventional polymer having a sol-gel transition temperature in an aqueous solution thereof, and reversibly assuming a sol state at a temperature lower than the above transition temperature is simply delivered into a vascular lumen, the following problems are posed:

1) If the polymer such as Pluronic F-127 is once converted into a gel state at the sol-gel transition temperature or above, the resultant gel is dissolved when water is further added thereto. That is, even if the polymer is converted into a gel state in a vascular lumen the blood dissolves the gel, and the polymer cannot maintain a stable gel state for a long period of time. As a result, the polymer cannot be effectively used to occlude the aneurysms, vascular tumors or vascular malformation.

2) The polymer has a sol-gel transition temperature higher than the temperature of the blood (about 37° C.), and therefore the polymer is not converted into a gel state in the vascular lumen, whereby the polymer cannot be used to occlude the aneurysms, vascular tumors or vascular malformation.

3) It is necessary to increase the concentration of the polymer in an aqueous solution thereof to an extremely high value, in order to convert the polymer into a gel state.

In the description appearing hereinafter, "%" (percent) and "part(s)" for describing quantities or ratios thereof are by weight unless otherwise noted specifically.

Sol-Gel Transition Temperature

In the present invention, the terms "sol state", "gel state" and "sol-gel transition temperature" are defined in the following manner.

With respect to these definitions, a publication (Polymer Journal, 18(5), 411-416 (1986)) may be referred to.

One ml of a solution of a polymer is poured into a test tube having an inside diameter of one cm, and is left standing for 12 hours in a water bath that is controlled at a predetermined (constant) temperature. In a case where the interface (meniscus) between the solution and air is deformed (inclusive of the case where the solution flows out from the test tube) due to the weight of the solution per se when the test tube is inverted, the above polymer solution is defined as being in a "sol state" at the above-mentioned predetermined temperature.

On the other hand, in a case where the interface (meniscus) between the solution and air is not deformed due to the weight of the solution per se even when the test tube is inverted, the polymer solution is defined as being in a "gel state" at the above-mentioned predetermined temperature.

When a polymer solution having a concentration of, e.g., about 3 wt. % is measured with the above method, and the temperature at which the "sol state" is converted into the "gel state" is determined while gradually increasing the above "predetermined temperature" (e.g., in 1° C. increments), the thus determined transition temperature is defined as the "sol-gel transition temperature". Alternatively, it is also possible to determine the temperature at which the "gel state" is converted into the "sol state" while gradually decreasing the "predetermined temperature" (e.g., in 1° C. decrements)

In the present invention, the sol-gel transition temperature is preferably higher above O° C. but not higher than 40° C. (more preferably, not lower than 4° C. and not higher than 37° C.) in view of the balance between the stability of the intralumenal implant (gel state) within a vascular lumen and easy delivery of the intralumenal implant (sol state) into the vascular lumen. The polymer having such a preferred sol-gel transition temperature may easily be selected from specific compound as described below, according to the above-mentioned screening method (method of measuring the sol-gel transition temperature).

In the intralumenal implant material, it is preferred to set the above-mentioned sol-gel transition temperature (a° C.) between the temperature at which a intralumenal implant based on such a polymer is to be delivered into a vascular lumen (b° C.; e.g., the temperature of an aqueous solution of the material), and the temperature of blood (c° C.). In other words, the above-mentioned three temperature points of a° C., b° C. and c° C. may preferably have a relationship of b<a<c. More specifically, the value of (a−b) may preferably be 1-35° C., more preferably 2-30° C. On the other hand, the value of (c−a) may preferably be 1-35° C., more preferably 2-30° C.

Plurality of Blocks Having Cloud Point

The plurality of blocks having a cloud point may preferably comprise a polymer that shows a negative solubility-temperature coefficient with respect to water. More specifically, such a polymer may preferably be one selected from the group of: polypropyleneoxide, copolymers comprising propyleneoxide and another alkylene oxide, poly-N-substituted acrylamide derivatives, poly-N-substituted methacrylamide derivatives, copolymers comprising an N-substituted acrylamide derivative and an N-substituted methacrylamide derivative, polyvinylmethylether, and partially-acetylated product of polyvinyl alcohol.

It is preferred that the above polymer block having a cloud point has a cloud point of higher than O° C. but not higher than 40° C., in view of the provision of a polymer comprising a plurality of blocks having a cloud point, and a plurality of hydrophilic block bonded thereto to be preferably used in the present invention having a sol-gel transition temperature of higher than O° C. and not higher than 40° C.

It is possible to measure the cloud point, e.g., by the following method. An aqueous solution (about 1 wt. %) of the polymer is cooled to be converted into a transparent homogeneous solution, and thereafter the temperature of the solution is gradually increased (temperature increasing rate: about 1° C./min.), and the point at which the solution first shows a cloudy appearance is defined as the cloud point.

Blocks can be monomers which show an appropriate cloud point or can be multiples (polymers) of such monomers. Specific examples of the poly-N-substituted acrylamide derivatives and poly-N-substituted methacrylamide derivatives which show cloud points are listed below:
Poly-N-acryloylpiperidine
Poly-N-propylmethacrylamide
Poly-N-isopropylacrylamide
Poly-N-diethylacrylamide
Poly-N-isopropylmethacrylamide
Poly-N-cyclopropylacrylamide
Poly-N-acryloylpyrrolidine
Poly-N,N-ethylmethylacrylamide
Poly-N-cyclopropylmethacrylamide
Poly-N-ethylacrylamide The above polymer may be either a homopolymer or a copolymer comprising a monomer constituting the above polymer and "another monomer". The "another monomer" to be used for such a purpose may be a hydrophilic monomer, or a hydrophobic monomer. In general, when copolymerization with a hydrophilic monomer is conducted, the resultant cloud point temperature may be increased. On the other hand, when copolymerization with a hydrophobic monomer is conducted, the resultant cloud point temperature may be decreased.

Accordingly, a polymer having a desired cloud point (e.g., a cloud point of higher than 0° C. and not higher than 40° C.) may be obtained by selecting monomers to be used for copolymerization.

Specific examples of the above hydrophilic monomers include: N-vinyl pyrrolidone, vinylpyridine, acrylamide, methacrylamide, N-methylacrylamide, hydroxyethylmethacrylate, hydroxyethylacrylate, hydroxymethylmethacrylate, hydroxymethylacrylate, methacrylicacid and acrylicacid having an acidic group, and salts of these acids, vinylsulfonicacid, styrenesulfonicacid, etc., and derivatives having a basic group such as N,N-dimethylaminoethylmethacrylate, N,N-diethylaminoethyl methacrylate, N,N-dimethylaminopropylacrylamide, salts of these derivatives, etc. However, the hydrophilic monomer to be usable in the present invention is not restricted to these specific examples.

On the other hand, specific examples of the above hydrophobic monomer may include acrylate derivatives and methacrylate derivatives such as ethylacrylate, methylmethacrylate, and glycidylmethacrylate; N-substituted alkymethacrylamide derivatives such as N-n-butylmethacrylamide; vinylchloride, acrylonitrile, styrene, vinyl acetate, etc. However, the hydrophobic monomer to be usable in the present invention is not restricted to these specific examples.

Hydrophilic Block

On the other hand, specific examples of the hydrophilic block to be combined with (or bonded to) the above-mentioned block having a cloud point may include: methyl cellulose, dextran, polyethyleneoxide, polyvinylalcohol, poly-N-vinylpyrrolidone, polyvinylpyridine, polyacrylamide, polymethacrylamide, poly-N-methylacrylamide, polyhydroxymethylacrylate, polyacrylicacid, polymethacrylicacid, polyvinylsulfonicacid, polystyrenesulfonicacid, and salts of these acids; poly-N,N-dimethylaminoethylmethacrylate, poly-N,N-diethylaminoethylmethacrylate, poly-N,N-dimethylaminopropylacrylamide, and salts of these, etc.

Method for Combining Cloud Point and Hydrophilic Blocks

The process for combining the above block having a cloud point with the hydrophilic block is not particularly limited. For example, it is possible to conduct such a combination by introducing a polymerizable functional group (such as acryloyl group) into either one of the above blocks, and copolymerizing with the resultant product a monomer capable of providing the other block.

Alternatively, it is also possible to obtain a combination product of the above block having a cloud point with the hydrophilic block by copolymerizing a monomer capable of providing the block having a cloud point with a monomer capable of providing the hydrophilic block. In addition, the block having a cloud point and the hydrophilic block may also be combined or bonded with each other by preliminarily introducing reactive functional groups (such as hydroxyl group, amino group, carboxyl group, or isocyanate group) into both kinds of the blocks, and combining these blocks by using an appropriate chemical reaction as is known to those of ordinary skill in the art of polymer chemistry. At this time, it is usual to introduce a plurality of reactive functional groups into the hydrophilic block.

Further, the polypropyleneoxide cloud point block and the hydrophilic block may be combined or bonded with each other by repetitively subjecting polypropyleneoxide and a monomer (such as ethyleneoxide) to a stepwise or consecutive polymerization, thereby obtaining a block copolymer comprising polypropyleneoxide and the another water-soluble polymer (such as polyethyleneoxide) combined therewith. Such a block copolymer may also be obtained by introducing a polymerizable group (such as acryloyl group) into the terminal functional group of polypropyleneoxide, and then copolymerizing therewith a monomer constituting the water-soluble polymer.

Further, a polymer usable in the present invention may be obtained by introducing a functional group which is reactive in a bond-forming reaction with the terminal functional group of polypropyleneoxide (such as hydroxyl group) into a water-soluble polymer, and reacting the resultant water-soluble polymer and the polypropyleneoxide.

In addition, a polymer usable in the present invention may be obtained by connecting polymers such as one comprising polypropyleneglycol and polyethyleneglycol bonded to both terminals thereof (such as Pluronic F-127; trade name). At a temperature lower than the cloud point, the inventive polymer (a compound comprising a plurality of blocks having a cloud point, and at lest one hydrophilic block combined therewith) may completely be dissolved in water so as to assume a sol state, since the "blocks having a cloud point" present in the polymer molecule is water-soluble together with the hydrophilic block at that temperature.

However, when a solution of the above polymer is heated to a temperature equal to or above the cloud point, the "blocks having a cloud point" present in the polymer molecule become hydrophobic so that separate molecules of the polymer are associated or aggregated with each other due to hydrophobic interactions. On the other hand, the hydrophilic block(s) is water-soluble even at this elevated temperature, and therefore, the polymer according to the present invention forms a hydrogel The hydrogel has a three-dimensional network structure wherein hydrophobic associations between the blocks having a cloud point constitute crosslinking points and interaction between water molecules and the hydrophilic blocks keeps the polymer from precipitating from solution.

When the hydrogel is again cooled to a temperature below the cloud point, the cloud point block becomes water-soluble and the crosslinking due to the hydrophobic association are released so that the hydrogel structure disappears, whereby the polymer again becomes an aqueous solution.

Thus, the sol-gel transition in the polymer according to the present invention is based on the reversible hydrophilic-hydrophobic conversion in the block having a cloud point present in the polymer molecule at the cloud point, and therefore the transition is completely reversible in response to a temperature change.

Intralumenal Implant

As described above, intralumenal implant according to the present invention comprising at least a polymer having a sol-gel transition temperature in an aqueous solution thereof, substantially shows a water insolubility at a temperature (d° C.) higher than the sol-gel transition temperature, and reversibly shows water solubility at a temperature (e° C.) lower than the sol-gel transition temperature. The above-mentioned temperature (d° C.) may preferably be a temperature which is at least 1° C., more preferably at least 2° C. (particularly preferably, at least 5° C.) higher than the sol-gel transition temperature.

Further, the above-mentioned "substantial water insolubility" may preferably be a state wherein the amount of the above polymer to be dissolved in 100 ml of water at the above temperature (d° C.) is 5.0 g or less (more preferably 0.5 g or less, particularly preferably 0.1 g or less). On the other hand, the above-mentioned temperature (e° C.) may preferably be a temperature which is at least 1° C., more preferably at least 2° C. (particularly preferably, at least 5° C.) lower than the sol-gel transition temperature.

Further, the above-mentioned "water solubility" may preferably be a state wherein the amount of the above polymer to be dissolved in 100 ml of water at the above temperature (e° C.) is 0.5 g or more (more preferably 1.0 g or more). The above "to show a reversible water solubility" refers to a state wherein an aqueous solution of the above polymer shows the above-described water solubility at a temperature lower than the sol-gel transition temperature, even when it is once formed into a gel state (at a temperature higher than the sol-gel transition temperature).

A 10%-aqueous solution of the above polymer may preferably show a viscosity of 10-3,000 centipoises, (more preferably, 50-1,000 centipoises) at 5° C. Such a viscosity may preferably be measured, e.g., under the following measurement conditions:

Viscometer: Stress-controlled type rheometer (model: CSL-500, manufactured. by Carri-Med. Co., USA)
Rotor diameter: 60 mm
Rotor configuration: Parallel-plate type
Measurement frequency: one Hz (hertz)

Even when the an aqueous solution of the polymer according to the present invention is formed into a gel state at a temperature higher than the sol-gel transition temperature, and thereafter the resultant gel is immersed in a large amount of water, the gel is not substantially dissolved in water. For example, such a characteristic of the above polymer may be confirmed in the following manner.

More specifically, 0.15 g of the polymer according to the present invention is dissolved in 1.35 g of distilled water at a temperature lower than the above sol-gel transition temperature (e.g., under cooling with ice) thereby to prepare a 10 w %-aqueous solution. The resulting solution is poured into a plastic Petri dish having a diameter of 35 mm, the dish is warmed to a temperature of 37° C. to form a gel having a thickness of about 1.5 mm in the dish, and the total weight of the Petri dish (f gram) containing the gel is measured.

Then, the entire Petri dish containing the gel is left standing in 250 ml of water at 37° C. for 10 hours, and thereafter the total weight of the Petri dish (g gram) containing the gel is measured to determine whether the polymer has been dissolved from the gel surface or not. At this time, in the polymer according to the present invention, the ratio of weight decrease in the gel, i.e., the value of $\{(f-g)/f\}$ may preferably be 5.0% or less, more preferably 1.0% or less (particularly preferably 0.1% or less).

Even when an aqueous solution of the polymer according to the present invention was converted into a gel state at a temperature higher than the sol-gel transition temperature, and the resultant gel was then immersed in a large volume of water (about 0.1-100 times larger than the gel, by volume ratio), the gel did not dissolve even over a long period of time (as shown by Example 3 appearing hereinafter).

On the contrary, in a case where a similar gel was formed by using the above-described Pluronic F-127 comprising polypropyleneoxide and polyethyleneoxide bonded to both terminals thereof, the resultant gel was completely dissolved when the gel is left standing in water for several hours.

The above-described property of the polymer according to the present invention is important in view of the long-term occlusion of the aneurysms, vascular and tumors vascular malformation. The properties of the polymer according to the present invention may be provided, e.g., by using a polymer having a plurality of blocks having a cloud point in one molecule as described above.

According to the present inventors' findings, in the case of the above-described Pluronic F-127, it is presumed that one molecule thereof has only one block having a cloud point (i.e., polypropyleneoxide block) present therein, and the crosslinking structure between hydrophobic groups to be formed at temperature higher than the sol-gel transition temperature is weak or fragile, and therefore the gel based on the Pluronic F-127 is dissolved in water.

On the other hand, in the case of the polymer according to the present invention, it is presumed that a gel having a firm crosslinking structure is formed because the polymer used therein has two or more hydrophobic blocks in one molecule, and the water-resistance of the resultant gel is thereby improved. The intralumenal implant according to the present invention comprises at least the above-described polymer having a sol-gel transition temperature, but may further comprise other components as desired.

Specific examples of the "other components" in such an embodiment may include e.g., biologically active substances, substances which modulate the sol-gel transition temperature of the polymer or the viscosity of the aqueous solution of the polymer and radiopaque substances.

Biologically Active Substances

In the present invention, it is preferred to use a cytokine and/or an extracellular matrix material having an effect of increasing the affinity with tissue and simultaneously promoting endothelialization. More specifically, preferred examples thereof may include e.g., extracellular matrixes such as various type of collagens, fibronectin, vitronectin, laminin, proteoglycan, and glycosaminoglycan. Cytokines such as TGF (tumor growth factor), FGF (fibroblast growth factor), VEGF (vascular endothelial growth factor), and PDGF (platelet-derived growth factor) can also be used. In addition to the extracellular matrix material or cytokine, thermally denatured products of collagen such as gelatin have a similar effect, and, therefore, these substances may also be used similarly as the above-described extracellular matrix, etc. Also, antineoplastic agents such as cisplantinum, carboplatinum, methotrexate, ACNU (1-4-amino-2-methyl-5-pyrimidinyl)-methyl-3-(2-chloroethyl)-3-nitroso urea) and BCNU (1,3-bis(2-chloroethyl)-1-nitrosourea) may be used. A variety of microtubule altering agents such as vincristine, vinblastine, colchicine, and water-soluble taxol derivatives are useful, too.

Sol-Gel Transition Temperature and Viscosity Modulators.

For modulation of the sol-gel transition temperature of the polymer or of the viscosity of the aqueous solution of the polymer, organic solvents, inorganic salts, surfactants, urea and amino acids may be used. Especially the substances that increase the sol-gel transition temperature or decrease the viscosity of the aqueous solution of the polymer are preferably used in the present invention for the easy endovascular or percutaneous delivery of the aqueous solution of the polymer into a vascular lumen.

Radiopaque Substances

The conventional insoluble radiopaque agents such as the powder of tungsten, tantalum, gold, platinum, barium sulfate and soluble radiopaque materials such as organoiodine compounds used in vascular and neurovascular radiology can be included in the polymer solution of the present invention. These agents are dissolved, suspended or emulsified into the solution.

In a case where the above-described biologically active substance and or substances which modulate the sol-gel transition temperature or the viscosity of the aqueous solution of the polymer, etc., are incorporated into the intralumenal implant material according to the present invention, for example, it is possible to adopt a method wherein such substances are dissolved or dispersed in an aqueous solution of the above polymer at a temperature lower than the sol-gel transition temperature of the polymer.

In the intralumenal implant according to the present invention, it is also possible to use an aqueous medium such as physiological saline solution, Ringer's solution, buffer, and culture medium, instead of the water to dissolve the other components. The intralumenal implant material according to the present invention may also contain, in addition to the above polymer and water, a liquid substance other than water. Specific examples usable for such a purpose may include: e.g., water-soluble liquids including alcohols (e.g., monohydric, dihydric and trihydric alcohols) such as ethanol, ethylene glycol, propylene glycol, and glycerin; oily liquids such as vegetable oil, liquid paraffin, and animal oil (an oily liquid is used after it is converted into a suspension or emulsion as desired). Radiopaque oils are but another example of possible additions to the mixture of the present invention. In a case where such a liquid substance is added, it is preferred to use the liquid in an amount of about 0.1-100 parts, more preferably about 1-50 parts with respect to 100 parts of water.

Method of Using the Intralumenal Implant Material

Described below is a preferred method of actually using the intralumenal implant material of to the present invention. At a temperature lower than the sol-gel transition temperature of the polymer constituting the intralumenal implant material, the polymer is dissolved in an aqueous medium such as water, physiological saline solution, Ringer's solution, or culture medium so as to provide a concentration of 2.0%-35% (more preferably 5.0%-30%).

At this time, it is also possible to add biologically active substances, substances which modulates the sol-gel transition temperature, or the viscosity of the aqueous solution of the polymer and/or a radiopaque agent, etc. to the aqueous solution of the above-described polymer, as desired.

Then, the resulting aqueous solution of the polymer is maintained at a temperature lower than the sol-gel temperature, and is endovascularly or percutaneously delivered into a vascular lumen while being maintained in the aqueous solution state. Generally, the desired site in a vascular lumen is accessed with a catheter. For a small diameter torturous vessel, a catheter may be guided to site through the use of a guide wire.

Once the site has been reached removing the guide wire clears the catheter lumen. The catheter may be flushed with cold physiological saline solution, etc. into the lumen of the catheter to prevent solidification of the polymer. Preferably, a double lumen catheter is used to cool down the injection system to below the sol-gel transition temperature of the polymer. Cold physiological saline is flushed through the outer lumen until the intralumenal implant material actually reaches the site of injection through the inner lumen of the catheter. In the percutaneous delivery, a double lumen needle may be preferably used in a similar manner as the above-described double lumen catheter.

The present invention will now be described in more detail with reference to Examples. However, it should be noted that the present invention is defined by Claims, and is not limited by the following Examples.

EXAMPLE 1

One hundred and sixty moles of ethyleneoxide were subjected to an addition reaction with one mole of trimethylol propane by cationic polymerization, thereby to obtain polyethyleneoxide triol. Of this polyethyleneoxide triol 0.02 moles were dissolved in 100 ml of distilled water, and then 0.1 moles of potassium permanganate was added thereto. The resulting mixture was subjected to an oxidization reaction at 25° C. for 60 minutes, thereby to obtain a polyethyleneoxide tricarboxyl derivative.

Ten grams of the polyethyleneoxide tricarboxyl derivative, 5 g of polypropyleneoxide diamino derivative (average propyleneoxide polymerization degree: about 65, Jeffamine D-4000, manufactured. by Jefferson Chemical Co., U.S.A.) and 5 g of both terminal-aminated polyethyleneoxide (molecular weight=6000, manufactured. by Kawaken Fine Chemical K.K.) were dissolved in 1000 ml of carbon tetrachloride, and then 1.2 g of dicyclohexyl carbodiimide was added thereto. The resulting mixture was allowed to react for 6 hours under boiling refluxing conditions.

The resulting reaction mixture was cooled and filtered, and thereafter the solvent was distilled off under reduced pressure. Then, the resulting residue was dried under vacuum, thereby to obtain a polymer (BPE) for an intralumenal implant material according to the present invention.

The above-described polymer BPE was dissolved in distilled water under cooling with ice so as to provide a concentration of 8%. When the resulting aqueous solution was gradually warmed, it was found that the viscosity thereof was gradually increased as the temperature rose above 5° C., and the solution was converted into a hydrogel at about 10° C. When the resulting hydrogel was cooled, it was converted back into an aqueous solution state at 5C. Such an aqueous solution (sol)-gel conversion could be observed reversibly and repetitively.

EXAMPLE 2

N-isopropylacrylamide (9.61 g) (manufactured. by Kojin K.K.), 0.14 g of n-butyl methacrylate (manufactured. by Wako Junyaku Kogyo K.K.), and 1.12 g of methacryloyl isocyanate (manufactured. by Nippon Paint K.K.) were dissolved in 400 ml of chloroform contained in a reaction vessel.

After the inside of the reaction vessel was purged with nitrogen gas, 0.135 g of N, NÅL-azobisisobutyronitrile was added thereto, and the resulting mixture was subjected to polymerization at 60° C. for 6 hours.

The reaction mixture was concentrated, and then was reprecipitated in diethyl ether to agglomerate precipitate particles. The resulting precipitate was dried under vacuum, thereby to obtain 7.8 g of poly (N-isopropylacrylamide-co-methacryloyl isocyanate-co-n-butylmethacrylate).

Then, 1.0 g of the thus obtained poly (N-isopropylacrylamide-co-methacryloyl isocyanate-co-n-butylmethacrylate) and 0.5 g of both terminal-aminated polyethylene oxide (molecular weight=6000, manufactured. by Kawaken Fine Chemical K.K.) were dissolved in 100 ml of chloroform, and the resulting mixture was allowed to react at 50° C. for 3 hours.

The reaction mixture was cooled to room temperature, and thereafter 0.1 g of isopropylamine was added thereto, and was left standing for 1 hour. The reaction mixture was concentrated, and then was precipitated in diethyl ether.

The resulting precipitate was separated by filtration, and then dried under vacuum, thereby to obtain 1.5 g of a polymer (GYM) for the intralumenal implant material according to the present invention.

GYM (0.5 g) was dissolved in 10 ml of distilled water under cooling with ice. When the resulting aqueous solution was gradually warmed, it was found that the solution lost its fluidity at about 30° C. or above and was converted into a gel state.

When the resulting gel was cooled, it recovered its fluidity at about 30° C. or below and was again converted into an aqueous solution. Such a sol-gel transition conversion was reversibly and repetitively observed. The above polymer had a sol-gel transition temperature of about 30° C.

EXAMPLE 3

An aqueous solution (a intralumenal implant material according the present invention) of the BPE obtained in Example 1 was converted into a gel state, and then immersed in a large amount of water at 37° C., whereby the dissolution characteristic of the resulting gel was measured with the elapse of time. Separately, as a comparative experiment, the above-described Pluronic F-127 (hereinafter, simply referred to as "F-127") was similarly converted into a gel, and the dissolution characteristic of the resultant gel was measured in water at 37° C.

More specifically, the above-described dissolution characteristic was evaluated in the following manner. That is, 0.15 g of the polymer (BPE) synthesized in Example 1 was dissolved in 1.35 g of distilled water under cooling with ice, thereby to prepare an aqueous solution having a concentration of 10%. Thereafter, the resulting solution was poured into a plastic Petri dish having a diameter of 35 mm, then the dish was warmed up to a temperature of 37'° C. to form a gel having a thickness of about 1.5 mm in the dish, and the total weight of the Petri dish (initial weight) containing the gel was measured.

Then, the entire Petri dish containing the gel was immersed in 250 ml of water at 37° C. for a predetermined period of time. Thereafter the Petri dish was taken out of the water, and the total weight of the Petri dish containing the gel was measured with the elapse of time, thereby to determine the difference between the measured weight and the above-described initial weight. In this manner, the dissolution behavior of the gel (from the gel surface being in contact with water) into water was evaluated.

As comparative experiments, each of 0.3 g and 0.45 g of the above F-127 was dissolved in 1.2 g or 1.05 g of distilled water, respectively, under cooling with ice, thereby to prepare an aqueous solution of the F-127 having a concentration of 20% and 30%, respectively. By using the thus obtained aqueous solutions, the dissolving behaviors of these aqueous solutions were evaluated in the same manner as in the case of the above BPE, by preparing a gel having a thickness of about 1.5 mm in a Petri dish, and leaving it standing in 250 ml of water at 37° C.

The results obtained by these experiments are shown in the graph of FIG. 1. It was considered that the above-described dissolution experiments simulated the dissolution behavior of the gel in blood, when the gel was placed in a vascular lumen. As shown in the above FIG. 1, in any of the cases of the Pluronic F-127 gels having concentrations of 20% and 30%, respectively, the gels were completely dissolved in water within several hours. On the other hand, in case of the gel of the intralumenal implant (BPE) according to the present invention, it was found that the gel was not substantially dissolved within 10 weeks.

These results of the experiments suggest that in the case of the Pluronic F-127, the resulting gel would be very unstable in a vascular lumen, but in the case of the intralumenal implant material according to the present invention, the resulting gel could remain stable after being placed in a vascular lumen.

EXAMPLE 4

An animal experimentation was conducted in accordance with policies set by National Institutes of Health guidelines. Two swine were used in this preliminary study. The swine were 3 to 4 months old, weighed 30 to 40 kg, were of mixed sex, and were maintained on a standard laboratory diet. After an overnight fast, each swine was premedicated with intramuscular 20 mg/kg of ketamine and 2 mg/kg of xylazine. General anesthesia was maintained with mechanical ventilation and inhalation of 1% to 2% halothane following endotracheal intubation.

The swine rete mirabile (RMB) is a fine network of arteries with connections across the midline to the contralateral RMB situated at the termination of each ascending pharyngeal artery as it perforates the skull base. This vascular network has some morphological similarities to a human plexiform AVM nidus, and it has previously been used for assessment of vascular histological responses of numerous embolic agents.

A 6 F guiding catheter was positioned in the left common carotid artery, using a transfemoral approach. An intra-arterial bolus injection of 3000 U of heparin was delivered. A 2.1 F microcatheter/microguidewire was positioned coaxially via the guiding catheter, with its tip located in the ascending pharyngeal artery, just proximal to the left RMB. The same polymer that prepared in Example 2 was used in this study. The delivery technique was as follows: 1) After a superselective angiogram was performed, 10 ml of saline (5-10° C.) were injected to flush the microcatheter; 2) 1.0 ml of polymer solution was aspirated into a 1 cc syringe; 3) The polymer was injected under fluoroscopic control until a total occlusion of the RMB and/or ascending pharyngeal artery was achieved.

Following a post embolization angiogram, the swine were sacrificed with an intravenous injection of pentobarbital (100 mg/kg). Each RMB and the brain were then surgically harvested from the skull base of each swine. The specimens were placed into 10% formalin for fixation. Sections were stained with hematoxylin and eosin and elastica van Gieson and studied microscopically.

Angiographical Findings

Figure 2A:
FIG. 2a shows a vascular structure prior to treatment with the present invention.
Figure 2B:
FIG. 2b shows the vascular structure of FIG. 2a following treatment with the material of the present invention.

All RMBs and ascending pharyngeal arteries were successfully occluded with the polymer (FIG. 2a compared to FIG. 2b). Total amounts of 0.5 to 1.0 ml of polymer were delivered through the microcatheter to the RMB and no difficulty was encountered in withdrawing the microcatheter after completing the embolization. Repeated embolizations of the polymer through the same microcatheter were performed without obstructing the microcatheter or gluing it in place. This polymer showed an appropriate fluoroscopic radio-opacity that allowed a controlled delivery in arteries as small as 250-400 μm in diameter. Post embolization clinical follow-ups showed no evidence of postembolization neurological deterioration or death.

Gross and Histopathological Findings

The embolized RMB and ascending pharyngeal arteries were soft and spongy and easy to harvest from skull base. No significant macroscopic abnormalities were seen in these specimens.

INDUSTRIAL APPLICABILITY

The present invention provides an intralumenal implant material which may be endovascularly or percutaneously delivered into a vascular lumen in a liquid state at the temperature lower than the sol-gel transition temperature may instantly be converted into a gel state so as to occlude aneurysms, vascular tumors or vascular malformation at the temperature higher than the sol-gel transition temperature (e.g. the blood temperature of about 37° C.). As described above, the intralumenal implant according to the present invention may provide a very easy delivery mode only by changing the temperature across the sol-gel transition temperature The intralumenal implant according to the present invention is biocompatible because the intralumenal implant material contains no toxic substances such as organic solvents and polymerizable monomers. The intralumenal implant according to the present invention will not mechanically injure the vascular tissue and the surrounding tissue due to the high flexibility of the water-containing gel constituting the intralumenal implant.

The intralumenal implant according to the present invention provides a very easy incorporation mode of biologically active substances into the intralumenal implant due to the common solvent, that is, water to both of the biologically active substance and the intralumenal implant.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method for occluding a vascular lumen comprising the step of injecting into said lumen an aqueous solution of an organic polymer having a gel-sol transition temperature wherein said aqueous solution forms a hydrogel at temperatures above said transition temperature, wherein each molecule of said polymer comprises a plurality of blocks, each of which has a cloud point, and at least one hydrophilic block covalently bonded with said plurality of blocks.

2. The method of claim 1, wherein said plurality of blocks are selected from the group consisting of N-acryloylpiperidine, N-propylmethacrylamide, N-isopropylacrylamide, N-diethylacrylamide, N-isopropylmethacrylamide, N-cyclopropylacrylamide, N-acryloylpyrrolidine, N-ethylmethylacrylamide, N-cyclopropylmethacrylamide, N-ethylacrylamide, propyleneoxide, alkeneoxide, vinylmethylether, and partially-acetylated vinyl alcohol.

3. The method of claim 1, wherein said hydrophilic block is selected from the group consisting of methyl cellulose, dextran, ethyleneoxide, vinyl alcohol, N-vinyl pyrrolidone, vinylpyridine, acrylamide, methacrylamide, N-methylacrylamide, hydroxyethylmethacrylate, hydroxyethylacrylate, hydroxymethyl methacrylate, hydroxymethylacrylate, methacrylicacid, acrylic acid, vinylsulfonic acid, styrenesulfonic acid, N,N-dimethylaminoethylmethacrylate, N,N-diethylaminoethyl methacrylate, and N,N-dimethylaminopropylacrylamide.

4. The method of claim 1, wherein said transition temperature is between 0° C. and 40° C.

5. The method of claim 1 further comprising adding biologically active substances to said organic polymer.

6. The method of claim 5, wherein the biologically active substances are selected from the group consisting of cytokines and extracellular matrix materials.

7. The method of claim 6, wherein the cytokines are selected from the group consisting of tumor growth factor, fibroblast growth factor, vascular endothelial growth factor and platelet-derived growth factor.

8. The method of claim 6, wherein the extracelluar matrix materials are selected from the group consisting of collagen, gelatin, fibronectin, vitronectin, laminin, proteoglycan, and glycosaminoglycan.

9. The liquid composition method of claim 5, wherein the biologically active substances further comprise antineoplastic agents.

10. The method of claim 1 further comprising adding radiopaque agents to said organic polymer.

11. The method of claim 10, wherein the radiopaque agents are selected from the group consisting of powdered tungsten, powdered tantalum, powdered gold, powdered platinum, barium sulfate and organoiodine compounds.

12. The method of claim 1, wherein said organic polymer further comprises substances which alter the gel-sol transition temperature.

13. The method of claim 1, wherein said organic polymer further comprises substances which alter viscosity of the aqueous solution.

\* \* \* \* \*